(12) United States Patent
Gunasekaran et al.

(10) Patent No.: US 9,851,308 B2
(45) Date of Patent: Dec. 26, 2017

(54) VISIBLE DETECTION OF MICROORGANISMS

(75) Inventors: Sundaram Gunasekaran, Madison, WI (US); Seok won Lim, Seoul (KR)

(73) Assignee: Wisconsin Alumni Research Foundation (WARF), Madison, WI (US)

( * ) Notice: Subject to any disclaimer, the term of this patent is extended or adjusted under 35 U.S.C. 154(b) by 0 days.

(21) Appl. No.: 13/300,148

(22) Filed: Nov. 18, 2011

(65) Prior Publication Data
US 2012/0129194 A1    May 24, 2012

Related U.S. Application Data

(60) Provisional application No. 61/415,498, filed on Nov. 19, 2010.

(51) Int. Cl.
| | | |
|---|---|---|
| G01N 21/78 | (2006.01) | |
| B82Y 30/00 | (2011.01) | |
| G01N 33/543 | (2006.01) | |

(52) U.S. Cl.
CPC .............. *G01N 21/78* (2013.01); *B82Y 30/00* (2013.01); *G01N 33/54346* (2013.01)

(58) Field of Classification Search
CPC ........ C12C 2537/143; C12C 2537/157; C12C 2545/00; C12C 2545/10; C12C 2563/131; C12C 2563/137; C12C 2563/143; C12C 2563/149; C12C 2563/155; C12C 2565/10; C12C 2565/101; C12C 2565/102; C12C 2565/113; C12C 2561/113
See application file for complete search history.

(56) References Cited

U.S. PATENT DOCUMENTS

| | | | |
|---|---|---|---|
| 6,620,627 B1 * | 9/2003 | Liberti et al. ................. | 436/526 |
| 2003/0092029 A1 | 5/2003 | Josephson et al. | |
| 2003/0143598 A1 * | 7/2003 | Garimella ............. | C07H 21/00 435/6.11 |
| 2005/0277159 A1 * | 12/2005 | Lehmann et al. ............. | 435/7.5 |
| 2008/0085508 A1 * | 4/2008 | Wei ...................... | G01N 33/587 435/5 |
| 2010/0173347 A1 | 7/2010 | Brook et al. | |
| 2012/0058548 A1 | 3/2012 | Huo et al. | |
| 2012/0156687 A1 | 6/2012 | Soman et al. | |

(Continued)

FOREIGN PATENT DOCUMENTS

| | | | | |
|---|---|---|---|---|
| WO | WO 2005/008222 | * | 1/2005 | ............ G01N 21/55 |
| WO | WO 2006/104979 | * | 10/2006 | |
| WO | 2012058627 | | 3/2012 | |

OTHER PUBLICATIONS

Osterfeld et al.,(PNAS. Dec. 2008. vol. 105(52): pp. 20637-20640).*

(Continued)

*Primary Examiner* — Ja'Na Hines
(74) *Attorney, Agent, or Firm* — Andrus Intellectual Property Law, LLP

(57) ABSTRACT

Methods of detecting very low levels of targets, such as cells, are provided. In some embodiments, for example, the methods can detect bacteria present in a sample at concentrations less than 25 cells/mL. The method involves detecting nanoparticle aggregation in the absence of the target.

13 Claims, 11 Drawing Sheets
(11 of 11 Drawing Sheet(s) Filed in Color)

(56) References Cited

U.S. PATENT DOCUMENTS

2012/0202218 A1  8/2012  Liedberg et al.

OTHER PUBLICATIONS

Asian et al., (J. of Phy. Chem. 2004. vol. 108. pp. 15631-15639).*

Chirathaworn, C. et al., "Detection of Leptospira in urine using anti-Leptospira-coated gold nanoparticles," (2011) Comparative Immunology, Microbiology and Infectious Diseases 34:31-34.

Fang, S.-B. et al., "Identification of Salmonella using colony-print and detection with antibody-coated gold nanoparticles," (2009) J. of Microbiological Methods 77:225-228.

Huang, S.-H., "Gold nanoparticle-based immunochromatographic test for identification of Staphylococcus aureus from clinical specimens," (2006) Clinica Chimica Acta 373:139-143.

Kamma, S. et al., "A rapid two dot filter assay for the detection of E. coli O157 in water samples," (2008) J. of Immunological Methods 336:159-165.

Lin, F. Y. H. et al., "Development of a Nanoparticle-Labeled Microfluidic Immunoassay for Detection of Pathogenic Microorganisms," (2005) Clinical and Diagnostic Laboratory Immunology 12(3):418-425.

Tallury, P. et al., "Nanobioimaging and sensing of infectious diseases," (2010) Advanced Drug Delivery Reviews 62:424-437.

Theron, J. et al., "Current molecular and emerging nanobiotechnology approaches for the detection of microbial pathogens," (2010) Critical Reviews in Microbiology 36(4):318-339.

Wang, S. et al., "Rapid colorimetric identification and targeted photothermal lysis of Salmonella bacteria by using bioconjugated oval-shaped gold nanoparticles," (2010) Chem. Eur. J. 16:5600-5606.

Chah, S. et al., "Gold nanoparticles as a colorimetric sensor for protein conformational changes," (2005) Chem. & Biol. 12:323-328.

Elghanian, R. et al., "Selective colorimetric detection of polynucleotides based on the distance-dependent optical properties of gold nanoparticles," (1997) Science 277:1078-1081.

Kalele, S. et al., "Rapid detection of Escherichia coli by using antibody-conjugated silver nanoshells," (2006) Small 2:335-338.

Lazcka, O. et al., "Pathogen detection: A perspective of traditional methods and biosensors," (2007) Biosens. Bioelectron. 22:1205-1217.

Li, X. et al., "Localized surface plasmon resonance (LSPR) of polyelectrolyte-functionalized gold-nanoparticles for bio-sensing," (2009) Colloids and Surfaces A: Physiocochem Eng. Aspects 332:172-179.

Njoki, P. et al., "Size correlation of optical and spectroscopic properties for gold nanoparticles," (2007) J. Phys. Chem. 111:14664-14669.

Sato, K. et al., Rapid aggregation of gold nanoparticles induced by non-cross-linking DNA hybridization (2003) J. Am. Chem. Soc. 125:8102-8103.

Wang, C. et al., "Gold nanorod probes for the detection of multiple pathogens," (2008) Small 4:2204-2208.

Wang, C. et al., "Multifunctional magnetic-optical nanoparticle probes for simultaneous detection, separation, and thermal ablation of multiple pathogens," (2010) Small 6:283-289.

Wilson, R., "The use of gold nanoparticles in diagnostics and detection," (2008) Chem. Soc. Rev. 37:2028-2045.

Zhao, X. et al., "A rapid bioassay for single bacterial cell quantitation using bioconjugated nanoparticles," (2004) PNAS 101(42):15027-15032.

* cited by examiner

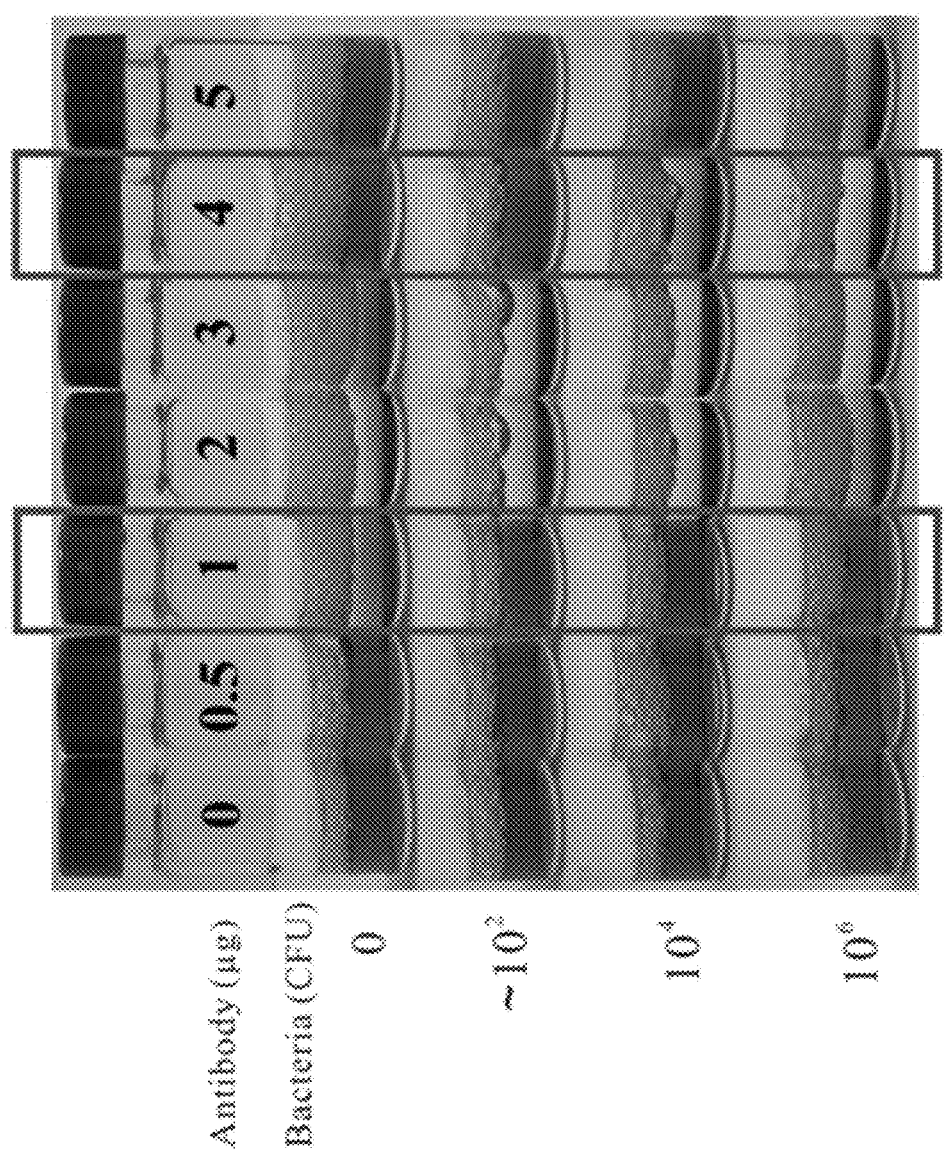

VISIBLE DETECTION OF MICROORGANISMS

This application claims the benefit of U.S. Provisional Application No. 61/415,498, filed Nov. 19, 2010, which is incorporated by reference herein in its entirety for any purpose.

BACKGROUND

The presence of even low levels of spoilage or pathogenic microorganisms in various products can be dangerous and even lethal. Therefore, sensitive, rapid, and simple-to-use methods for detecting microorganisms that can be performed in out-of-the-laboratory settings, and by untrained persons, are preferred over those requiring sophisticated techniques that are laborious, time consuming, or require skilled personnel to carry out. For example, the analysis of genetic information based on the polymerase chain reaction (PCR), a popular method for sensitive detection of bacteria, requires complicated sample preparation protocols performed by skilled personnel. Some alternative methods are known, such as detection of intact bacterial cells using specific antibody-antigen binding, but simple, fast, and sensitive methods are needed.

Since sol particle immunoassays (SPIA) were introduced, target-mediated (i.e., on-target) aggregation of gold nanoparticles (AuNPs) has been used to visually detect the occurrence of some biological events or the presence of small biomolecules such as proteins and DNA. However, using the principle of on-target aggregation of AuNPs for visual detection of large targets such as microorganisms, especially at extremely low concentrations, has proved difficult.

SUMMARY

In some embodiments, methods of determining whether a sample comprises a target are provided. In some embodiments, the method comprises (a) contacting the sample with a linker, wherein the linker comprises a first functionality and a plurality of second functionalities, wherein the first functionality is capable of binding to the target, and wherein each of the plurality of second functionalities is capable of binding to a third functionality; (b) contacting the sample from (a) with a plurality of nanoparticles, wherein each of the plurality of nanoparticles comprises a third functionality that is capable of binding to the second functionality; and (c) detecting nanoparticle aggregation in the sample from (b), wherein the absence of nanoparticle aggregation indicates that the sample comprises the target.

In some embodiments, the method comprises (a) contacting the sample with a linker, wherein the linker comprises a first functionality and a plurality of second functionalities, wherein the first functionality is capable of binding to the target, and wherein each of the plurality of second functionalities is capable of binding to a third functionality; (b) contacting the sample from (a) with a plurality of nanoparticles, wherein each of the plurality of nanoparticles comprises a third functionality that is capable of binding to the second functionality; and (c) detecting nanoparticle aggregation in the sample from (b), wherein the presence of nanoparticle aggregation indicates that the sample comprises the target. In some embodiments, the linker is present in an excess concentration relative to the concentration of the nanoparticles.

In some embodiments, the first functionality is selected from an antigen binding region of an antibody, a ligand, a receptor, a small molecule, and a lectin. In some embodiments, the second functionality is selected from biotin, streptavidin, an antigen, an antibody, a ligand, a receptor, a polyhistidine tag, nickel, an aptamer, an aptamers target, trans-cyclooctene, and tetrazine. In some embodiments, the third functionality is selected from biotin, streptavidin, an antigen, an antibody, a ligand, a receptor, a polyhistidine tag, nickel, an aptamer, an aptamers target, trans-cyclooctene, and tetrazine. In some embodiments, the second and third functionalities together form a binding pair selected from biotin/streptavidin, ligand/receptor, polyhistidine tag/nickel, aptamer/aptamer target, antibody/antigen, and trans-cyclooctene/tetrazine.

In some embodiments, the linker is an antibody and the first functionality is the antigen binding region of the antibody. In some embodiments, the second functionality is biotin and the third functionality is streptavidin.

In some embodiments, the nanoparticles are selected from gold nanoparticles, silver nanoparticles, platinum nanoparticles, magnetite nanoparticles, gold/iron alloy nanoparticles, and latex nanoparticles. In some embodiments, the target is selected from prokaryotic cells, eukaryotic cells, and parasites.

In some embodiments, detecting nanoparticle aggregation comprises determining at least one characteristic selected from sample color, UV-VIS spectrum, UV-VIS peak wavelength, and absorbance. In some embodiments, the at least one characteristic of the sample from (b) is compared to at least one characteristic of a standard. In some embodiments, the standard is a control reaction comprising the linker and the plurality of nanoparticles, but not the target. In some embodiments, the standard is a representation of at least one characteristic of a control reaction that comprises the linker and the plurality of nanoparticles, but not the target.

In some embodiments, kits for determining whether a sample comprises a target are provided. In some embodiments, a kit comprises (i) a linker, wherein the linker comprises a first functionality and a plurality of second functionalities, wherein the first functionality is capable of binding to the target, and wherein each of the plurality of second functionalities is capable of binding to a nanoparticle; and (ii) a plurality of nanoparticles, wherein each of the plurality of nanoparticles comprises a third functionality that is capable of binding to the second functionality.

In some embodiments, the first functionality is selected from an antigen binding region of an antibody, a ligand, a receptor, a small molecule, and a lectin. In some embodiments, the second functionality is selected from biotin, streptavidin, an antigen, an antibody, a ligand, a receptor, a polyhistidine tag, nickel, an aptamer, an aptamers target, trans-cyclooctene, and tetrazine. In some embodiments, the third functionality is selected from biotin, streptavidin, an antigen, an antibody, a ligand, a receptor, a polyhistidine tag, nickel, an aptamer, an aptamers target, trans-cyclooctene, and tetrazine. In some embodiments, the second and third functionalities together form a binding pair selected from biotin/streptavidin, ligand/receptor, polyhistidine tag/nickel, aptamer/aptamer target, antibody/antigen, and trans-cyclooctene/tetrazine. In some embodiments, the nanoparticles are selected from gold nanoparticles, silver nanoparticles, platinum nanoparticles, magnetite nanoparticles, gold/iron alloy nanoparticles, and latex nanoparticles.

In some embodiments, the linker is an antibody and the first functionality is the antigen binding region of the antibody. In some embodiments, the second functionality is biotin and the third functionality is streptavidin.

In some embodiments, a kit further comprises a standard. In some embodiments, the standard is a representation of at least one characteristic of a control reaction that comprises the linker and the plurality of nanoparticles, but not the target. In some embodiments, the at least one characteristic is selected from sample color, UV-VIS spectrum, UV-VIS peak wavelength, and absorbance.

BRIEF DESCRIPTION OF THE FIGURES

This patent application file contains at least one drawing executed in color. Copies of this patent application publication with color drawings will be provided by the Office upon request and payment of the necessary fee.

FIG. 1A shows the color of the reactions containing *E. coli* concentrations of $10^1$ to $10^9$ CFU/400 µL (tubes 1 to 9, respectively). FIG. 1B shows the control reaction (left tube) and the reaction containing $10^9$ CFU/400 µL (right tube) after centrifugation.

FIG. 2A shows the control reaction (right tube) and the reaction containing $10^9$ CFU/400 µL (left tube) using the original concentration of AuNPs after centrifugation. FIG. 2B shows the control reaction (right tube) and the reaction containing $10^9$ CFU/400 µL (left tube) using 25% of the original concentration of AuNPs after centrifugation.

FIG. 3A shows binding of AuNPs to the cell surface through a biotinylated antibody linker. FIG. 3B shows aggregation of AuNPs following cross-linking of multiple AuNPs through the biotinylated antibody.

FIG. 4A shows the color difference between samples containing *E. coli* (red, right tube) and not containing *E. coli* (purplish, left tube) after 15 minutes. FIG. 4B shows the same samples after one hour. FIG. 4C shows the UV-VIS spectra of samples containing $10^1$ to $10^7$ CFU/mL *E. coli*, as described in Example 4. The peak absorbance wavelength for each trace is indicated by an arrow.

FIG. 11 shows photographs of assay reactions in the presence of various concentrations of bacteria and various concentrations of biotinylated antibody, as described in Example 6. The red boxes indicate two exemplary biotinylated antibody concentrations that provided sensitive detection of low levels of bacteria.

DETAILED DESCRIPTION

Figure 1:
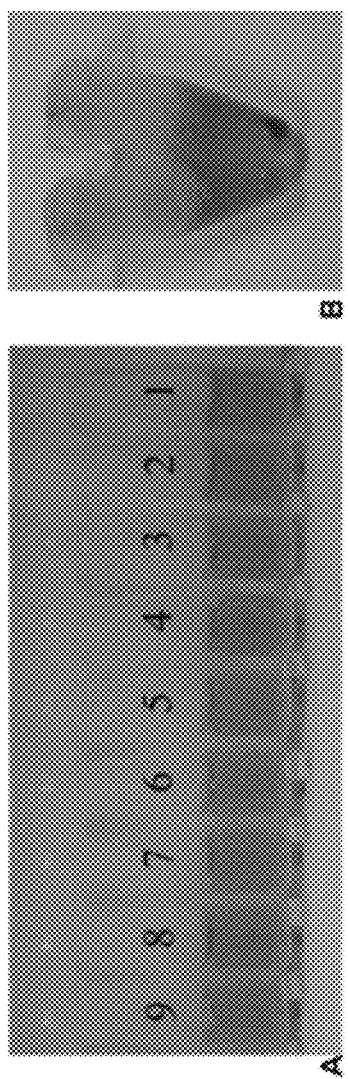
FIG. 1 shows the results of on-target detection of bacteria using antibody-conjugated gold nanoparticles (AuNPs), as described in Example 2.

The present invention provides a novel strategy for detection of targets, such as cells. In this strategy, the aggregation of nanoparticles does not occur in the presence of the target, but rather indicates the absence of the target. The method uses a bifunctional linker that comprises a first functionality that binds to a target, and a second functionality that facilitates aggregation of nanoparticles. When the linker is bound to the target, aggregation of the nanoparticles does not occur to a significant extent. In the absence of target, however, the linker is available to facilitate aggregation of the nanoparticles. Aggregation of the nanoparticles can be detected through changes in at least one characteristic of the sample. For example, in some embodiments, aggregation causes the color of the sample changes. Further, the present method is effective for detecting targets that are much larger than the nanoparticles, such as cells, and is very sensitive— the method can detect *E. coli* concentrations of less than 25 cells/mL. In addition, the reagents used in the present method can be designed such that they provide a desired level of specificity for one or more targets. That is, in some embodiments, reagents can be designed such that the method detects, for example, a particular target (such as a particular strain of bacteria). In some embodiments, reagents can be designed such that the method detects, for example, two or more targets (such as two or more strains of bacteria), e.g., by binding to a functionality that is shared among the two or more targets, or by mixing together reagents that are specific for each target to be detected, or a combination of the two methods.

Definitions

The terms "bifunctional linker" and "linker" are used interchangeably herein to refer to a molecule that comprises a first functionality that binds to a target, and a second functionality that is capable of binding to at least one nanoparticle. In some embodiments, a linker comprises a plurality of second functionalities. In some embodiments, a second functionality is capable of binding to a plurality of nanoparticles.

The term "nanoparticles," as used herein, refers to particles that are less than 1 µm in diameter and which cause a detectable change in a sample when they aggregate. Nanoparticles may be of any shape, including spherical and rod-shaped, so long as the longest dimension is within the diameter thresholds discussed herein. In some embodiments, a nanoparticle is less than 0.5 µm, less than 0.1 µm, less than 50 nm, less than 10 nm, less than 5 nm in diameter. In some embodiments, nanoparticles are functionalized with a moiety (referred to herein as a "third functionality") that interacts with the second functionality of a linker, described above. The term "nanoparticles" includes nanoparticles that are functionalized with such a moiety.

The term "target," as used herein, refers to an entity that is to be detected. In some embodiments, a target is greater than 0.1 µm in its longest dimension. In some embodiments, a target is greater than 0.5 µm, greater than 1 µm, greater than 2 µm, or greater than 5 µm in its longest dimension.

Exemplary Linkers

The methods described herein use a linker comprising a first functionality that is capable of binding to a selected target, and a second functionality that is capable of binding to at least one nanoparticle. In some embodiments, a second functionality is capable of binding to a plurality of nanoparticles. In some embodiments, the linker comprises a plurality of second functionalities. In some embodiments, the linker facilitates the aggregation of the nanoparticles. For example, in some embodiments, a linker comprising a plurality of second functionalities brings a plurality of nanoparticles in close proximity such that they aggregate. In some embodiments, the linker comprises a single second functionality, wherein the second functionality is capable of binding to a plurality of nanoparticles. In some such embodiments, the second functionality brings a plurality of nanoparticles in close proximity such that they aggregate.

The first functionality, in some embodiments, is any moiety that is capable of binding to the target. In some embodiments, multiple first functionalities are capable of binding to a single target. Nonlimiting exemplary first functionalities include antigen binding regions of antibodies, ligands, receptors, small molecules, and lectins (such as mannose-binding lectins), etc. When the first functionality is an antigen binding region of an antibody, the linker may comprise the entire antibody, or just a portion of the antibody that includes the antigen binding region. In some embodiments, when a first functionality is an antigen binding region of an antibody, the target comprises the antigen on its surface. In some embodiments, the target comprises multiple copies of the antigen on its surface such that a plurality of linkers can bind to a single target. In some embodiments, when a first functionality is a ligand, the target comprises the receptor on its surface. In some embodiments a first functionality binds to multiple targets, for example, when multiple different targets comprise the same or a similar antigen on their surfaces. One skilled in the art can select a suitable first functionality depending on the particular target(s) to be detected.

The second functionality, in some embodiments, is a member of a binding pair, wherein the nanoparticles comprise the other member of the binding pair (in some embodiments, a third functionality). Nonlimiting exemplary binding pairs include biotin/streptavidin, ligand/receptor, polyhistidine tag/nickel, aptamer/aptamer target, antibody/antigen, trans-cyclooctene/tetrazine (see, e.g., Haun et al., *Nat. Nanotechnol.* 5(9): 660-6 (2010)), etc. One skilled in the art can select a suitable second functionality and/or third functionality depending on the linker, the nanoparticles, and the intended application.

In some embodiments, the linker comprises a plurality of copies of the second functionality. In some embodiments, the linker comprises at least 3, at least 4, at least 5, at least 6, at least 7, at least 8, at least 9, at least 10, at least 15, or at least 20 copies of the second functionality.

In some embodiments, a second functionality is capable of binding to multiple copies of the third functionality. In some embodiments, a second functionality is able to bind to at least 3, at least 4, at least 5, at least 6, at least 7, at least 8, at least 9, or at least 10 copies of the third functionality. In some such embodiments, a linker may comprise one or just a few copies of the second functionality.

Nonlimiting exemplary linkers may comprise proteins, peptides, nucleic acids, aptamers, small molecules, carbohydrates, polymers, binding pairs, etc. In some embodiments, one or more portions of the protein, peptide, nucleic acid, aptamer, small molecule, carbohydrate, polymer, etc., acts as the first functionality and/or the second functionality of the linker. For example, in some embodiments, a linker may comprise a biotinylated protein, wherein the protein is a ligand for a particular receptor on the surface of a target cell, and the nanoparticles are functionalized with streptavidin. In some such embodiments, the first functionality of the linker is the ligand portion of the protein (which may be the entire protein) and the second functionality is biotin. In some embodiments, a linker is a biotinylated antibody. In some such embodiments, the antigen binding region is the first functionality and biotin is the second functionality.

Exemplary Nanoparticles

Nonlimiting exemplary nanoparticles include gold nanoparticles, silver nanoparticles, platinum nanoparticles, magnetite nanoparticles, gold/iron alloy nanoparticles, and latex nanoparticles.

In some embodiments, nanoparticles have an average size of between 1 nm and 1 µm. In some embodiments, the nanoparticles are gold nanoparticles (AuNPs). In some embodiments, the gold nanoparticles have an average size of between 1 nm and 100 nm. In some embodiments, gold nanoparticles have an average size of between 1 nm and 50 nm, between 5 nm and 50 nm, between 5 nm and 30 nm, between 5 nm and 20 nm, or between 10 and 15 nm.

For a particular detection method, nanoparticles are selected that are smaller than the target to be detected. In some embodiments, the target is at least 10-fold, at least 20-fold, at least 30-fold, at least 50-fold, at least 100-fold, or at least 200-fold larger than the nanoparticles. As a nonlimiting example, in a method of detecting *E. coli*, which is about 1 to 3 µm in its longest dimension, nanoparticles may be selected for detection that are between 10 nm and 20 nm. One skilled in the art can select suitably sized nanoparticles depending on the target to be detected.

In some embodiments, nanoparticles are functionalized with (i.e., comprise) a member of a binding pair (in some embodiments, referred to as a third functionality). In some embodiments, the nanoparticles are functionalized with (i.e., comprise) a member of a binding pair that binds to the member of the binding pair comprised in the linker (i.e., the second functionality). Nonlimiting exemplary binding pairs are described in the "Exemplary Linker" section, above. In some embodiments, nanoparticles are functionalized with (i.e., comprise) streptavidin. One skilled in the art can select a suitable binding pair depending on the particular nanoparticles, linker, and application.

Methods of functionalizing nanoparticles are known in the art. In some embodiments, for example, nanoparticles are functionalized with streptavidin according to the method described in Example 1. One skilled in the art can select a suitable method of functionalizing nanoparticles depending on the particular application.

Exemplary Targets

The methods described herein can be used to detect targets that are greater than 0.1 µm in their longest dimension. In some embodiments, a target is greater than 0.2 µm, greater than 0.5 µm, greater than 1 µm, greater than 2 µm, or greater than 5 µm. Nonlimiting exemplary targets include prokaryotic cells (such as bacterial cells), eukaryotic cells (including yeast), parasites, etc. In some embodiments, a target is a microbial food and/or water contaminant.

Nonlimiting exemplary targets that can be detected using the methods described herein include *E. coli* (including *E. coli* 0157:H7), *Staphylococcus aureus*, *Salmonella* species (including *Salmonella enteritidis* and *Salmonella typhimurium*), *Clostridium botulinum, Pseudomonas aeruginosa, Campylobacter jejuni, Yersinia enterocolitica, Yersinia psudotuberculosis, Listeria monocyteogenes, Vibrio cholerae* (both O1 and non-O1), *Vibrio parahaemolyticus, Vibrio vulnificus, Clostridium perfringens, Bacillus cereus, Aeromonas hydrophila, Shigella, Streptococcus, Cryptosporidium, Giardia lamblia, Entamoeba histolytica, Cyclospora cayetanensis, Anisakis, Diphyllobothrium, Nanophyetus, Eustrongylides, Acanthamoeba, Ascaris lumbricoides, Trichuris trichiura, Legionella,* fecal coliforms, non fecal coliforms (such as *Enterobacter, Klebsiella, Citrobacter*), etc.

As discussed above, for a particular target, nanoparticles are selected such that the target is at least 10-fold, at least 20-fold, at least 30-fold, at least 50-fold, at least 100-fold, or at least 200-fold larger than the nanoparticles.

Exemplary Samples

The present methods can be used to detect targets in a variety of sample types, including water samples (such as drinking water, water used for irrigation, and waste water); food; biological samples (such as bodily fluids, pharmaceuticals, etc.); cosmetics; air samples; etc. In some embodiments, a sample is diluted, concentrated, suspended, and/or dissolved prior to, or during, the methods described herein. In some embodiments, a sample is at least partially separated prior to using it in the methods described herein, such as, for example, separating blood fractions. In some embodiments, a buffering agent is added to a sample prior to, or during, the methods described herein. In some such embodiments, the buffering agent is added to bring and/or maintain the sample at a particular pH during at least a portion of the method. One skilled in the art can prepare a sample for use in the present methods, depending on the state of the sample (i.e., liquid, solid, gel, paste, etc.), the thickness of the sample, the density of the sample, the pH of the sample, the predicted microbial concentration in the sample, etc.

Exemplary Methods of Detecting Targets

In some embodiments, methods of determining whether or not a sample comprises a target are provided. In some embodiments, the method comprises contacting the sample with a linker and nanoparticles and detecting aggregation of the nanoparticles. In some embodiments, aggregation of the nanoparticles indicates the absence of the target in the sample. In some embodiments, minimal or no aggregation of the nanoparticles indicates the presence of the target in the sample. In some such embodiments, the linker is present at a lower concentration than the nanoparticles.

In some embodiments, the method comprises contacting the sample with a linker and nanoparticles and detecting aggregation of the nanoparticles. In some embodiments, aggregation of the nanoparticles indicates the presence of the target in the sample. In some embodiments, minimal or no aggregation of the nanoparticles indicates the absence of the target in the sample. In some such embodiments, the linker is present at an excess concentration relative to the nanoparticles.

In some embodiments, the linker is added to a sample before the nanoparticles are added. In some such embodiments, if target is present in the sample, the linker binds to the target. If no target is present, the linker remains in solution. In some embodiments, nanoparticles are then added. If the linker is in solution, and not bound to the target, in some embodiments, the linker facilitates aggregation of the nanoparticles. If the linker is bound to target cells, in some embodiments, its ability to facilitate aggregation of the nanoparticles is impaired and little or no aggregation occurs. Thus, in some embodiments, the absence of the target is indicated by aggregation of the nanoparticles.

In some embodiments, the linker is present at an excess concentration relative to the nanoparticles. In some such embodiments, if no target is present, the excess linker prevents aggregation of the nanoparticles. In some embodiments, the linker is present at a concentration sufficient to prevent aggregation of the nanoparticles in the absence of target. In some embodiments, if target is present, sufficient linker is bound to the target such that the remaining linker in solution facilitates aggregation of the nanoparticles. Thus, in some such embodiments, the presence of the target is indicated by aggregation of the nanoparticles.

A sample to which linker and nanoparticles have been added is referred to, in some embodiments, as a "test sample."

In some embodiments, linker is added at a concentration such that a small number of targets will "soak up" most or all of the linker. In some embodiments, for example, if a linker is a biotinylated antibody, the linker is added at a concentration of between about 0.1 µg/mL and 100 µg/mL. In some embodiments, the linker is added at a concentration of between about 0.1 µg/mL and about 50 µg/mL. In some embodiments, the linker is added at a concentration of between about 0.1 µg/mL and about 25 µg/mL. In some embodiments, the linker is added at a concentration of between about 0.1 µg/mL and about 10 µg/mL. In some embodiments, the linker is added at a concentration of between about 0.1 µg/mL and about 3 µg/mL. In some embodiments, the linker is added at a concentration of between about 0.5 µg/mL and about 3 µg/mL. An appropriate linker concentration can be determined by one skilled in the art, considering such factors as the identity of the linker, the identity of the target, the number of binding sites for the first functionality on the target to be detected, the efficiency of binding to the target, the predicted number of targets in a sample, etc.

In some embodiments, linker is added at an excess concentration, such that a small number of targets will "soak up" some of the linker, leaving sufficient linker in solution to facilitate aggregation of the nanoparticles. In some such embodiments, for example, if a linker is a biotinylated antibody, the linker is added at a concentration of between about 0.1 µg/mL and 100 µg/mL. In some embodiments, the linker is added at a concentration of between about 1 µg/mL and about 100 µg/mL. In some embodiments, the linker is added at a concentration of between about 1 µg/mL and about 50 µg/mL. In some embodiments, the linker is added at a concentration of between about 1 µg/mL and about 25 µg/mL. In some embodiments, the linker is added at a concentration of between about 1 µg/mL and about 10 µg/mL. In some embodiments, the linker is added at a concentration of between about 2 µg/mL and about 10 µg/mL. In some embodiments, the linker is added at a concentration of between about 2 µg/mL and about 5 µg/mL. An appropriate linker concentration can be determined by one skilled in the art, considering such factors as the identity of the linker, the identity of the target, the number of binding sites for the first functionality on the target to be detected, the efficiency of binding to the target, the predicted number of targets in a sample, etc.

In some embodiments, nanoparticles are added at a concentration such that aggregation of the nanoparticles by the available linker is detectable above the background of non-aggregated nanoparticles. As a nonlimiting example, if gold nanoparticles between 10 nm and 15 nm in size are used to detect, e.g., *E. coli*, a concentration of nanoparticles between 1 nM to 20 nM, 5 nM to 15 nM, or between 5 nM and 10 nM may be used. An appropriate nanoparticle concentration can be determined by one skilled in the art, considering such factors as the type of nanoparticle, the identity of the linker, the identities of the second and third functionalities, the efficiency of binding of the second and third functionalities, the number of binding sites for the nanoparticles on the linkers, the concentration of linker in the test sample, etc. The concentration should be selected such that there is an observable difference between aggregated and non-aggregated nanoparticles.

In some embodiments, detection of aggregation is carried out by detecting a change in at least one characteristic of the test sample. In some embodiments, the change in at least one characteristic of the test sample is determined as a change from time 0, immediately after the nanoparticles are added, to a time T after incubation of the test sample. In some embodiments, time T is 5 minutes, 10 minutes, 15 minutes, 20 minutes, 25 minutes, 30 minutes, 35 minutes, 40 minutes, 45 minutes, 50 minutes, 55 minutes, 60 minutes, 70 minutes, 80 minutes, 90 minutes, 100 minutes, or 120 minutes. Thus, in some embodiments, a characteristic of the sample at time 0 is compared to the same characteristic of the sample at time T.

In some embodiments, the change in at least one characteristic of the test sample is determined by comparing the at least one characteristic of the test sample to one or more standards. In some embodiments, the standard is a control sample. In some embodiments, a control sample comprises the same linker and nanoparticles as the test sample, but does not contain the target. In some embodiments, the control sample has undergone the same processing as the test sample, although the processing of the control sample may or may not have occurred contemporaneously with the processing of the test sample.

In some embodiments, a standard is a representation of at least one characteristic of a test sample or a control sample. Such a representation may be of a sample that comprises the target, or a sample that lacks the target. In some embodiments, at least one characteristic of a test sample is compared to both a standard that represents the at least one characteristic in a sample that comprises the target, and a standard that represents the at least one characteristic in a sample that lacks the target.

Various characteristics of a test sample may be used to determine whether the nanoparticles have aggregated. Non-limiting exemplary characteristics include color, UV-visible spectrum, UV-visible peak wavelength, and absorbance.

In some embodiments, aggregation of nanoparticles causes a change in a test sample that is visible to the naked eye. In some embodiments, aggregation of nanoparticles causes a color change in a test sample. In some embodiments, for example, when gold nanoparticles are used, a test sample in which the nanoparticles have not aggregated is red in color, while a test sample in which the nanoparticles have aggregated is purple in color. In some embodiments, the peak wavelength of a test sample in which the nanoparticles (such as gold nanoparticles) have not aggregated is about 530 nm, while the peak wavelength of a test sample in which the nanoparticles have aggregated is about 550 nm to 560 nm, with increased absorption at wavelengths above 600 nm.

In some embodiments, the presence of aggregation in a test sample indicates that the target is not present at levels detectable by that particular assay. Thus, in some embodiments, if gold nanoparticles are being used in the method, and the test sample turns purplish over time and/or the peak UV-visible wavelength shifts from about 530 nm to 550 nm or longer, the sample does not contain a detectable amount of the target.

In some embodiments, the absence of aggregation in a test sample indicates that the target is present. Thus, in some embodiments, if gold nanoparticles are being used in the method, and the test sample remains red over time and/or the peak UV-visible wavelength remains at about 530 nm, the sample contains the target.

In some embodiments, the presence of aggregation in a test sample indicates that the target is present. Thus, in some embodiments, if gold nanoparticles are being used with an excess amount of antibody in the method, and the test sample turns purplish over time and/or the peak UV-visible wavelength shifts from about 530 nm to 550 nm or longer, the sample contains a detectable amount of the target.

In some embodiments, the absence of aggregation in a test sample indicates that the target is not present at levels detectable by that particular assay. Thus, in some embodiments, if gold nanoparticles are being used with an excess amount of antibody in the method, and the test sample remains red over time and/or the peak UV-visible wavelength remains at about 530 nm, the sample does not contain the target.

In some embodiments, the absorbance of the sample at a particular wavelength is detected with a colorimeter in order to detect aggregation. In some embodiments, a change in the absorbance at a particular wavelength indicates a change in the amount of aggregation in a sample, and the presence or absence of the target. In some embodiments, for example, for a system using gold nanoparticles and a limiting amount of an antibody to the target, if the absorbance at 530 nm is detected, and the absorbance decreases after addition of the sample, the sample does not contain a detectable amount of the target (i.e., aggregation occurs, and the peak wavelength shifts to 550 nm or longer, reducing the absorbance at 530 nm). In other embodiments, for example, for a system using gold nanoparticles and an excess amount of an antibody to the target, if the absorbance at 530 nm is detected, and the absorbance decreases after addition of the sample, the sample contains a detectable amount of the target (i.e., aggregation occurs, and the peak wavelength shifts to 550 nm or longer, reducing the absorbance at 530 nm).

In some embodiments, the color of the sample is determined using a histogram of a color image of the sample. In some embodiments, the color of the sample is determined using a Turboscan.

Exemplary Standards

In some embodiments, at least one characteristic of a test sample is compared to at least one characteristic of a standard. In some embodiments, a standard is a control sample that has been treated under the same conditions, and comprises the same linker and nanoparticles, as the test sample, but lacks the target. One skilled in the art can include a suitable control sample in a method if desired.

In some embodiments, a standard is a representation of at least one characteristic of a test sample. For example, in some embodiments, if the at least one characteristic is the color of the test sample, a standard may be a representation of one or more colors to which the test sample can be compared. In some embodiments, if the at least one characteristic is a UV-visible spectrum of the test sample, a standard may be a representation of a UV-visible spectrum that would be expected from a test sample comprising the target and/or a representation of a UV-visible spectrum that would be expected from a test sample that does not comprise the target. One skilled in the art can make and use a suitable standard according to the characteristic to be considered and the particular method employed.

Exemplary Kits

In some embodiments, kits are provided. In some embodiments, a kit comprises a linker and nanoparticles. In some embodiments, a kit further comprises at least one standard. Nonlimiting exemplary linkers, nanoparticles, and standards are described herein.

The following examples are offered by way of illustration and are not intended to limit the invention in any way.

EXAMPLES

Example 1

Materials and Methods

Deionized water, filtered at 18 MΩ·cm of resistivity, was used in all experiments. Most chemicals (hydrogen tetrachloroaurate, trisodium citrate, streptavidin, bovine serum albumin (BSA), borate buffer, phosphate buffered saline (PBS), HEPES buffer, glycerine and NaOH) were purchased from Fisher Scientific (Pittsburgh, Pa., USA) and used as received unless indicated otherwise. Biotin was purchased from Sigma-Aldrich (St. Louis, Mo., USA) and anti-tissue/cell preparation of $E.$ $coli$ polyclonal rabbit IgG antibody (pAb) (GTX13626) and biotinylated antibody (GTX40640) were from Genetex Inc. (Irvine, Calif., USA). DH5α $E.$ $coli$ was cultured in LB plates then gathered and diluted in PBS to obtain a $1\times10^{10}$ CFU/mL suspension, which was then diluted as needed.

Synthesis of Gold Nanoparticles (AuNPs)

AuNPs (13-nm average diameter) were prepared by adding 10% v/v of 1 trisodium citrate to a boiling solution of 1 mM hydrogen tetrachloroaurate. After the color of the solution turned wine red, the citrate-stabilized AuNPs were stirred until the solution cooled down to room temperature.

Functionalizing AuNPs with Antibody

AuNPs were functionalized with antibody by charge adsorption as follows. 500 µL of freshly prepared colloidal AuNPs was mixed with 400 µL borate buffer (pH 7.4), and then 100 µL of pAb solution (400 µg/mL in PBS) was added. After 10 min of incubation, the mixture was centrifuged and washed with borate buffer (pH 9.5) twice to remove unbound pAb. Centrifuged pAb-conjugated AuNPs were stored in 500 µL PBS/0.1% w/v sodium azide.

Functionalizing AuNPs with Streptavidin

AuNPs were functionalized with streptavidin by charge adsorption as follows. The streptavidin solution was prepared in borate buffer (pH 7.4) at 50 µg/mL. 400 µL of the streptavidin solution was mixed with 600 µL of freshly prepared colloidal AuNPs (estimated to be at a concentration of about 8 nM). Following 30 min of incubation, the streptavidin-coated AuNPs were centrifuged, the supernatant was removed, the streptavidin-coated AuNPs were washed several times, and then resuspended in 600 µL of PBS/0.1% bovine serum albumin.

The biotin-dependence of the aggregation of streptavidin functionalized AuNPs in the presence of biotinylated antibodies was confirmed as follows. 100 µL of 10 µg/mL biotin was added to 200 µL of streptavidin-coated AuNPs. After 15 minutes, 100 µL of biotinylated pAb was added to the biotin-treated AuNPs. No visible color change was observed, suggesting that the aggregation of the AuNPs is dependent on the binding of the streptavidin on the AuNPs to the biotinylated antibodies.

UV-vis Absorption Spectra

Absorption spectra were measured using a UV-vis spectrophotometer (UV-1601PC, Shimadzu, Columbia, Md., USA). For sample preparation, PBS was added to each reaction sample to a final volume of 1 mL.

Example 2

On-Target Detection Resulted in No Visible Color Change

To investigate the effect of attaching AuNPs on $E.$ $coli$ on the overall color of the sample solution, 200 µL of pAb-conjugated AuNPs were added to 200 µL of various concentrations of $E.$ $coli$ in PBS, for total $E.$ $coli$ concentrations of $10^1$ to $10^9$ CFU/400 µL. The samples were then incubated at room temperature for one hour. The attachment of AuNPs on $E.$ $coli$ was verified by examining the color of sediment obtained by lightly centrifuging the solution at 3000 rpm for 10 min.

The results of that experiment are shown in FIG. 1. Even at the highest concentrations of $E.$ $coli$ tested, no visually distinguishable color change was observed. See FIG. 1A. Following centrifugation, however, the presence of a dark-red sediment confirmed that the AuNPs were bound to the $E.$ $coli$. See FIG. 1B. However, the color of the supernatant remained unchanged. Compare tube on left (no $E.$ $coli$ control) with tube on the right ($10^9$ CFU/400 µL $E.$ $coli$). These results suggest that only a small fraction of the AuNPs in the sample is bound to the cell surface, and that this fraction is insufficient to cause a visible color change in the system.

Example 3

On-Target Detection with Lower Concentration of AuNPs Resulted in No Visible Color Change Next, the effect of lowering the initial AuNPs concentration was investigated. The AuNPs were diluted with PBS to a concentration of 25% of its original level. In addition, in this experiment, biotinylated antibody was first bound to the $E.$ $coli$, and then streptavidin-functionalized AuNPs were added. After binding of the biotinylated antibodies to $E.$ $coli$, the cells were washed multiple times to remove unbound antibodies.

For direct visual comparison of the sample color, all tests were performed under the same conditions, keeping sample volumes and particle concentrations the same. Samples were diluted in PBS to 200 µL, and then 200 µL of streptavidin-coated AuNPs was added to bind the AuNPs to pAb. For the control, the same procedure was followed without the biotinlyated pAb such that AuNPs would not specifically bind to the cell surface.

Figure 2:
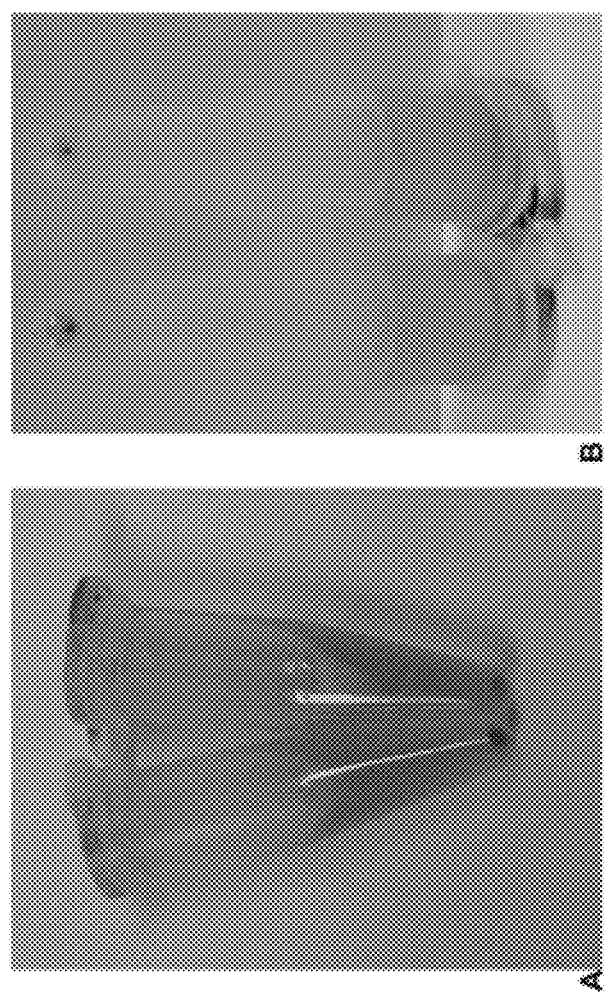
FIG. 2 shows the results of on-target detection of bacteria using an AuNP concentration that is 25% of the concentration used in the experiment shown in FIG. 1, as described in Example 3.

The results of that experiment are shown in FIG. 2. The binding of AuNPs to $E.$ $coli$ ($10^9$ CFU/400 µL) at both high and low concentrations of AuNPs was verified by examining the color of the centrifuged sediment. See FIG. 2. FIG. 2A shows samples containing higher a higher concentration of AuNPs (100% concentration). FIG. 2B shows samples containing a lower concentration of AuNPs (25% concentration). Although the color of the samples containing a lower AuNPs concentration was lighter, there was still no distinguishable change in the sample color upon binding of AuNPs to $E.$ $coli$. Compare sample on left (with biotinylated antibody) to sample of right (without biotinylated antibody) in FIG. 2B.

Figure 3:
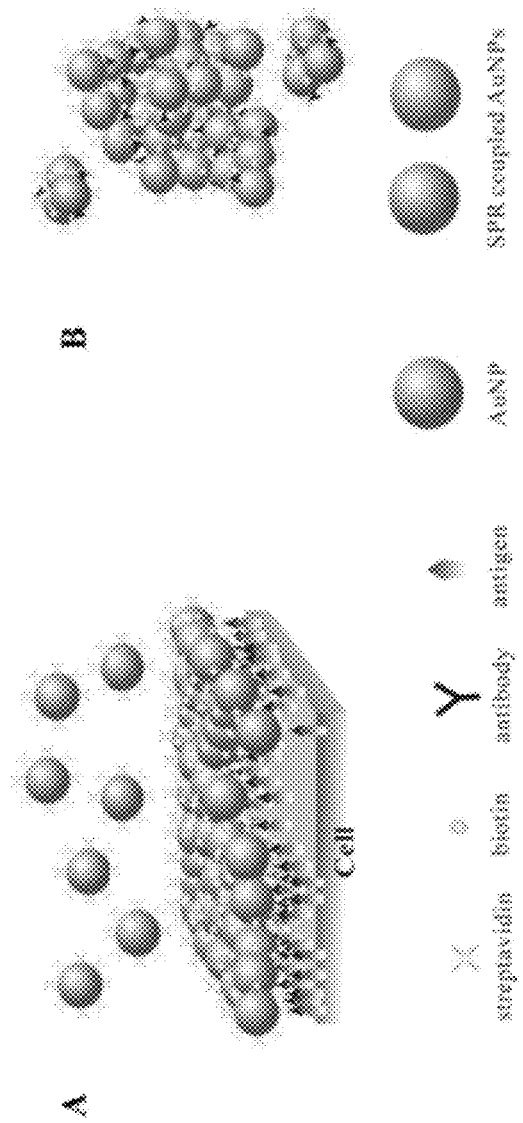
FIG. 3 shows a schematic of a proposed mechanism for off-target cell detection, as discussed in Example 4.

The above experiments further indicate that the binding of AuNPs directly to bacteria does not change the sample color sufficiently for on-target visual detection of bacteria. Without being bound by any particular theory, this result may be due to one or more of the following reasons. First, it may be that only a small fraction of the total AuNPs binds to the bacteria, even at a low initial AuNP concentration. Second, considering that AuNPs bind to bacteria at the antigen sites, uniform covering of AuNPs on the cell surface may be unlikely because antigen sites are not equally spaced and/or the relatively large AuNPs, compared to inter-antigen spacing, occlude several antigen sites on the cell surface. See FIG. 3A. Third, it may be that monolayered AuNP binding to the cell surface cannot produce a plasmonic effect strong enough for visual indication as would three-dimensional clusters of AuNPs that occur off-target. See FIG. 3B.

Example 4

Observable Color Change Using Off-Target Detection

Because on-target binding of AuNPs to cells did not result in a visible color change in the above experiments, the potential of detecting cells using off-target aggregation of AuNPs was investigated. According to the manufacturer, the biotinylated antibody is labeled with 7 to 10 biotins per unit. Therefore, one free antibody should be able to crosslink multiple strepavidin-coated AuNPs and facilitate color-changing aggregation of AuNPs. An unaggregated solution of AuNPs is red, and the color shifts to purple as the AuNPs aggregate. The ability of the biotinylated antibody to cause the color shift was confirmed by incubating the antibody with streptavidin-coated AuNPs, with and without excess biotin. Data not shown. In the absence of excess biotin, addition of biotinylated antibody to streptavidin-coated AuNPs results in a color change from red to purple. When excess biotin is added, which blocks the biotin binding sites on the streptavidin-coated AuNPs and prevents the biotinylated antibody from crosslinking the AuNPs, the color change does not occur.

To test the off-target detection of cells, 100 µL of $E.$ $coli$ suspended in PBS at $10^2$, $10^4$, $10^6$, and $10^8$ CFU/mL was mixed with 100 µL of 10 µg/mL biotin-conjugated antibody in PBS (resulting in $E.$ $coli$ concentrations of 10, $10^2$, $10^3$, and $10^4$ CFU/mL and 5 µg/mL antibody). The mixture was incubated for 30 minutes with vigorous stirring. After the incubation, 200 µL of streptavidin-coated AuNPs was added and the color change was monitored as a function of time.

Figure 4:
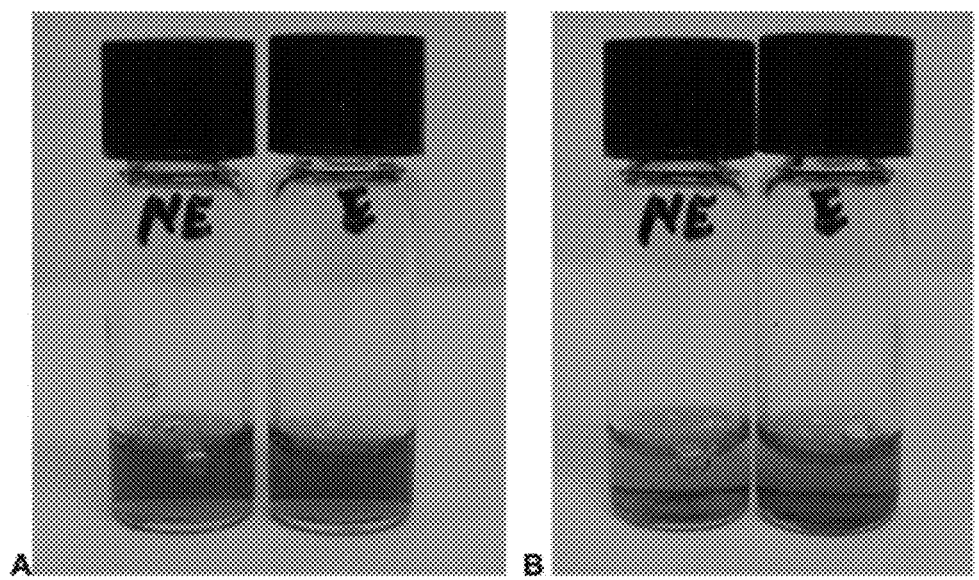
FIG. 4 shows the results of the off-target detection assay described in Example 4.
Figure 4:
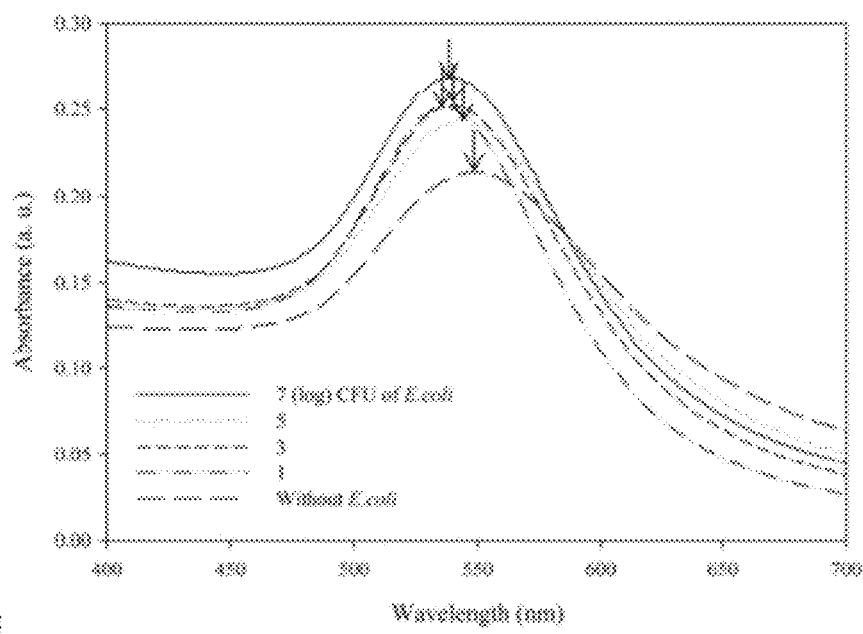

The results of that experiment are shown in FIG. 4. A visible color change from red to purple occurs within about 15 min. See FIG. 4A. At one hour, a more pronounced color change is observed. See FIG. 4B. While the color change is not directly proportional to the $E.$ $coli$ concentration, a shift in the UV-VIS peak absorbance is evident when $E.$ $coli$ are present. See FIG. 4C. Accordingly, at the very least, this off-target method produced a yes/no indication of the presence of bacteria in this experiment, even at $E.$ $coli$ concentrations as low as 10 CFU/mL.

Similar experiments were carried out with $Pseudomonas$ $aeruginosa$ and $Salmonella$ $typhimurium$, demonstrating that the off-target detection method can detect a range of targets.

Example 5

Characteristics of AuNP Aggregation

In order to examine the color-changing characteristics of AuNP aggregation as a function of target concentration, an assay system was designed using streptavidin-coated AuNPs and biotinylated BSA.

Figure 5:
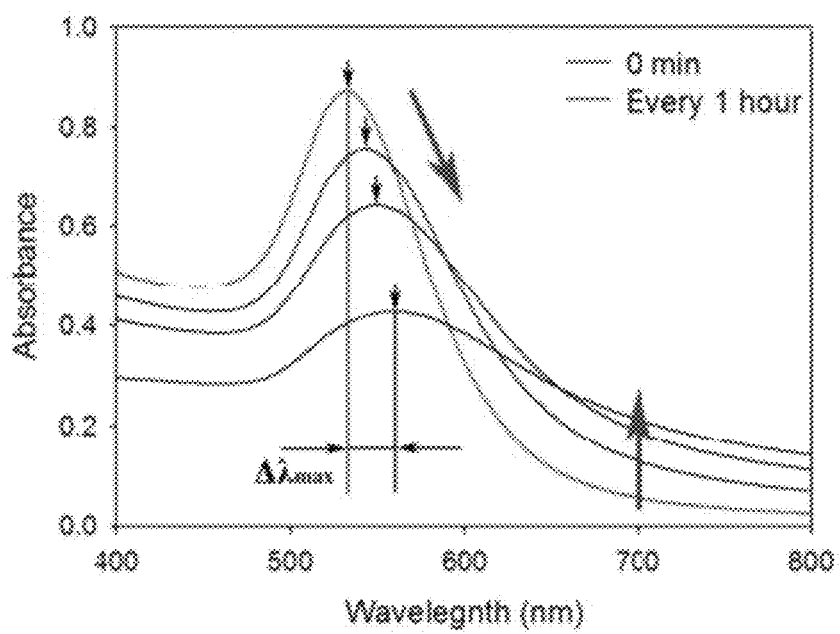
FIG. 5 shows the peak absorbance change and peak wavelength shift in a mixture containing biotinylated BSA and streptavidin-coated AuNPs, as described in Example 5.

Biotinylated BSA (Sigma-Aldrich; 0.5 µg in 100 µl) was mixed with 200 µl streptavidin-coated AuNPs made as described in Example 1, in a total volume of 400 µl (brought up to volume with PBS). The mixture was incubated at room temperature (~10° C. to 30° C.). The absorption spectrum of the mixture was taken at 0 hour, 1 hour, 2 hours, and 3 hours to determine the absorbance and peak wavelength changes of the mixture over time, as the streptavidin-coated AuNPs bind to the biotinylated BSA. As shown in FIG. 5, the peak absorbance of the mixture decreased with time, while the peak absorption wavelength increased. At the same time that the peak absorbance decreased, the absorbance at higher wavelengths increased (see large arrows in FIG. 5). These changes indicate that the streptavidin-coated AuNPs were aggregating in the presence of the biotinylated BSA.

Figure 6A:
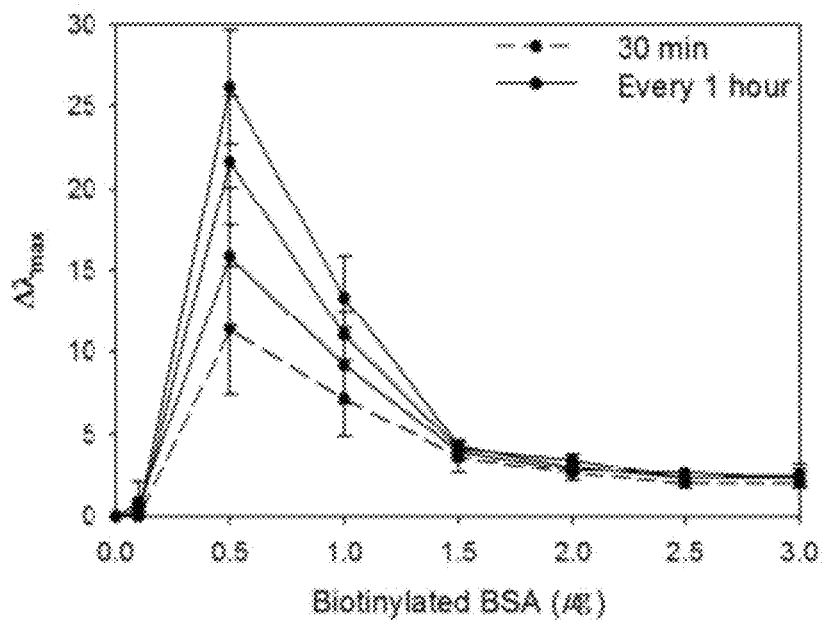
FIG. 6 shows (A) a plot of ΔλMax versus biotinylated BSA concentration for mixtures of biotinylated BSA and streptavidin-coated AuNPs at various time points; (B) a photograph of the mixtures from (A) at the 3 hour time point, with an indication of the regions exemplified in (C); and (C) a schematic showing an exemplary mechanism explaining the phenomena observed at different concentrations of biotinylated BSA; as described in Example 5.
Figure 6B:
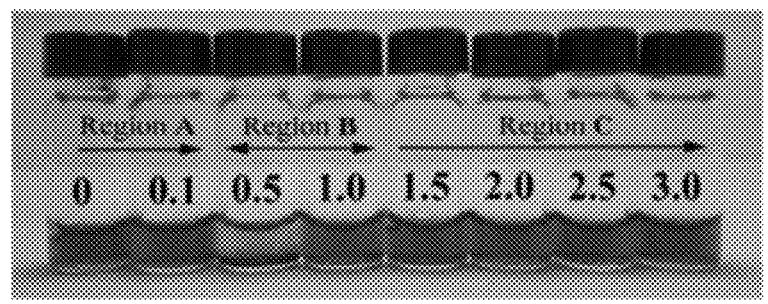
Figure 6C:
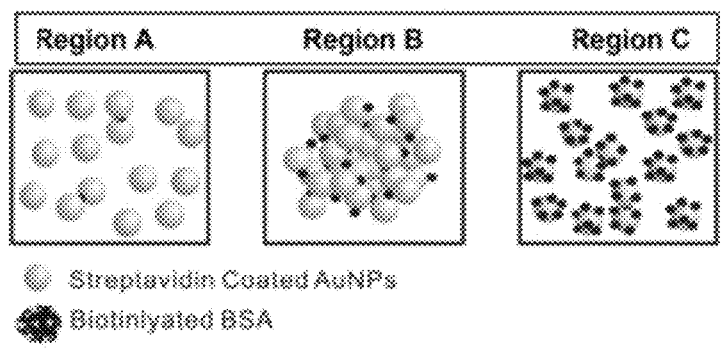
Figure 7:
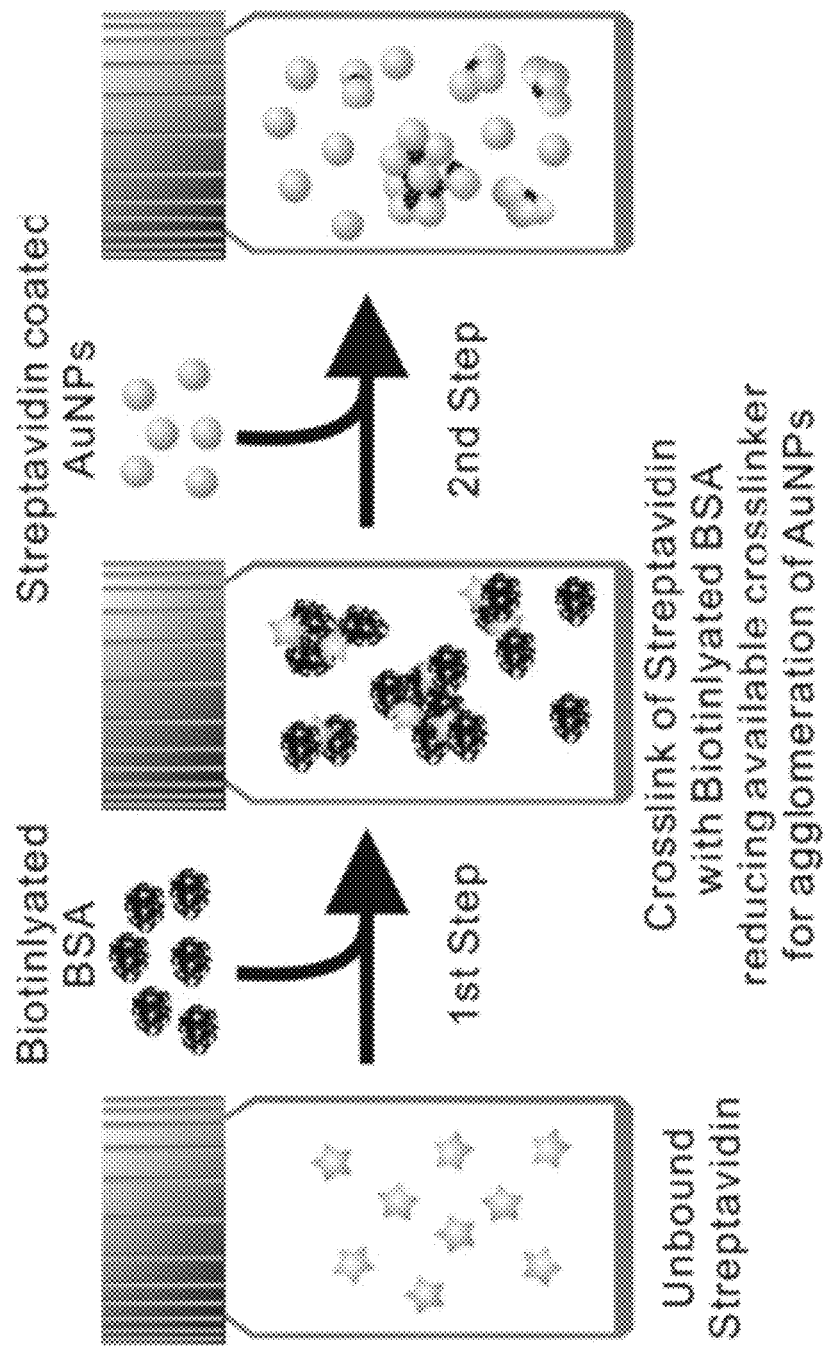
FIG. 7 is a diagram of the method involving pre-incubation with free streptavidin, as described in Example 5.
Figure 8:
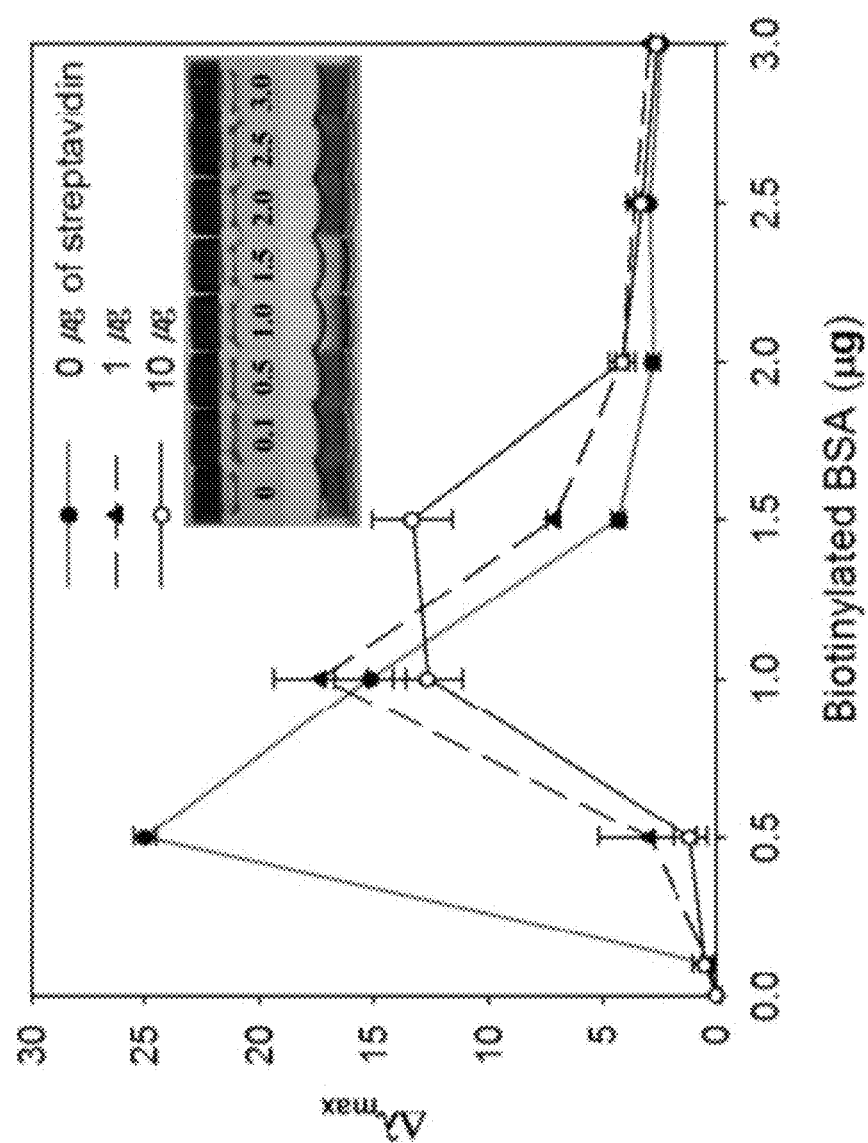
FIG. 8 shows a plot of ΔλMax versus biotinylated BSA concentration for mixtures of biotinylated BSA and streptavidin-coated AuNPs in the presence of various concentrations of free streptavidin, as described in Example 5. The inset shows photographs of the mixtures in the presence of 10 µg streptavidin.

The relationship between the concentration of biotinylated BSA and the change in the peak absorbance over time was then investigated. Increasing amounts of biotinylated BSA in 100 µl (0.5, 1, 1.5, 2, 2.5, and 3 ng/100 µl) were incubated with 200 of streptavidin-coated AuNPs in a total volume of 400 µl (brought up to volume with PBS), and the mixture was incubated at room temperature. The absorption spectrum of each mixture was taken at 30 minutes, 1 hour, 2 hours, and 3 hours, and the $\Delta\lambda$max measured from each time point to the next, at each concentration of biotinylated BSA. The results of that experiment are shown in FIG. 6A. The greatest peak wavelength changes over time occurred at the lower amounts, or concentrations, of biotinylated BSA. At the lowest concentration of biotinylated BSA (e.g., 0.1 µg in this experiment), there is insufficient biotinylated BSA to aggregate the AuNPs, so they remain in solution with no wavelength change over time. At the "middle" concentrations of biotinylated BSA (e.g., 0.5 µg and 1 µg in this experiment), there is sufficient biotinylated BSA to aggregate the AuNPs, resulting in peak wavelength changes over time. At higher concentrations of biotinylated BSA (e.g., 1.5 µg and greater in this experiment), there is excess biotinylated BSA and aggregation does not occur because there is sufficient biotinylated BSA to coat each AuNP. These regions are shown in FIG. 6B (lowest concentrations=Region A; "middle" concentrations=Region B; highest concentrations=Region C) and illustrated in FIG. 6C. The effect of free streptavidin on the color change observed in FIG. 6B was determined. A schematic representation of the assay is shown in FIG. 7. A similar experiment as described above for FIG. 6 was carried out, but in the presence of 0 µg streptavidin, 1 µg streptavidin, or 10 µg streptavidin. Free streptavidin was incubated with the biotinylated BSA prior to addition of the AuNPs. Each mixture was incubated at room temperature for 2 hours before the absorption spectrum was taken. The $\Delta\lambda$max was measured from each time point to the next, at each concentration of biotinylated BSA. The results of that experiment are shown in FIG. 8. The addition of free streptavidin caused the greatest $\Delta\mu$max to shift to a higher concentration of biotinylated BSA. In other words, more biotinylated BSA was required to aggregate the streptavidin-coated AuNPs in the presence of free streptavidin. Compare, e.g., FIG. 8 inset to FIG. 6B.

Figure 9:
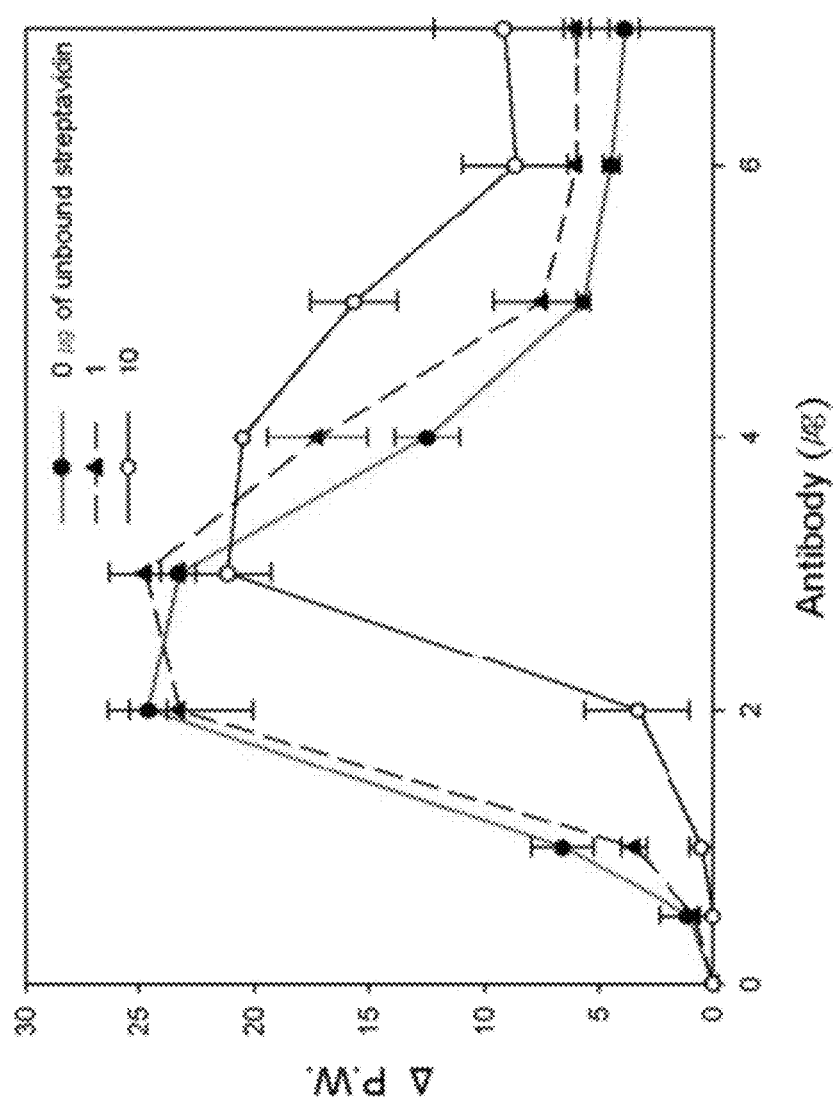
FIG. 9 shows a plot of ΔλMax versus biotinylated antibody concentration for mixtures of biotinylated antibody and streptavidin-coated AuNPs in the presence of various concentrations of free streptavidin, as described in Example 5.

A similar experiment was carried out using various concentrations of biotinylated antibody, preincubated with 10 μg, 1 μg, or 10 μg free streptavidin, and then mixed with 200 μl of streptavidin-coated AuNPs, in a total volume of 400 μl (brought up to volume with PBS). The results of that experiment are shown in FIG. 9. Briefly, the antibody concentration at which the greatest Δλmax shifted from 2 μg biotinylated antibody (in the presence of 0 or 1 μg streptavidin) to 3 to 4 μg antibody (in the presence of 10 μg streptavidin).

Example 6

Sensitivity of Off-Target Microorganism Detection Using AuNPs

Figure 10:
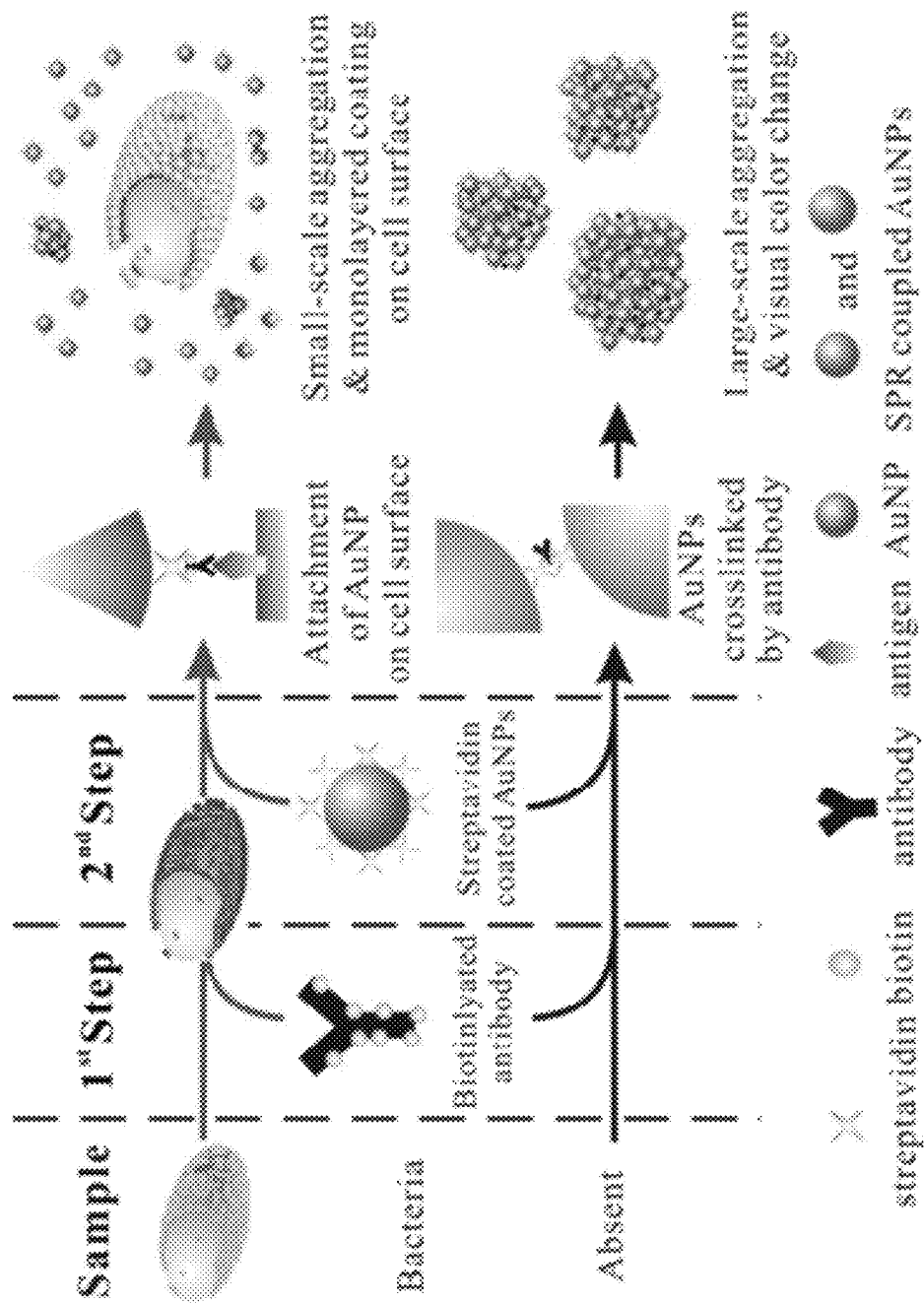
FIG. 10 shows an exemplary method of detecting microbial contamination in a sample, as described in Example 6.

An exemplary method and model for off-target microbial detection using AuNPs is shown in FIG. 10. Briefly, in a first step, a sample that may or may not comprise a microorganism is incubated with biotinylated antibodies that bind, for example, to a marker on the surface of the microorganism. If microorganisms are present, the biotinylated antibodies bind to the surface of the microorganisms. In a second step, strepatavidin-coated AuNPs are added to the sample. If there are no microorganisms in the sample, the biotinylated antibody cross-links the biotinylated AuNPs and large-scale aggregates form, causing a visual color change in the sample from red to purple. If microorganisms are present, the streptavidin-coated AuNPs bind to the biotinylated antibodies on the surface of the microorganisms, preventing large-scale aggregation of the AuNPs and the color change.

In order to determine the potential sensitivity of the off-target detection assay illustrated in FIG. 10, the assay was carried out using a range of biotinylated antibody concentrations (0, 0.5, 1, 2, 3, 4, and 5 μg in 100 μl) and a range of bacterial concentrations (0, $10^2$, $10^4$, and $10^6$ CFUs in 100 μl), with 200 μl streptavidin-coated AuNPs (total final volume of 400 μl). The mixtures were incubated at room temperature for 2 hours.

The results of that experiment are shown in FIG. 11. In this experiment, it was demonstrated that two different color change phases can be observed. At 1 μg biotinylated antibody, indicated by the first red box, the streptavidin-coated AuNPs are aggregated in the absence of bacteria (0 CFU), and the color of the mixture is purple. This aggregation occurs because the biotinylated antibody concentration to streptavidin-coated AuNP concentration is such that there is less biotinylated antibody than streptavidin-coated AuNP, allowing multiple streptavidin-coated AuNPs to bind to each biotinylated antibody, which results in aggregation. With just 100 CFUs of bacteria present, the biotinylated antibodies are bound to the surface of the bacteria and no longer aggregate the streptavidin-coated AuNPs, resulting in a red color. At 4 μg biotinylated antibody, indicated by the second red box, the AuNPs are not aggregated in the absence of bacteria (0 CFU) because there is an excess of biotinylated antibody (see, e.g., FIG. 6C, "Region C"). With $10^4$ CFUs of bacteria present, however, aggregation begins to occur because much of the biotinylated antibody is "soaked up" by the bacteria, leaving enough biotinylated antibody in solution to aggregate the streptavidin-coated AuNPs.

Thus, the present system can be fine-tuned to a very high level of sensitivity for a particular threshold of microbial contamination. For example, in some embodiments, for testing a sample in which little or no microbial contamination can be tolerated, such as food or pharmaceuticals, a lower amount of biotinylated antibody is used, and the system will be purple in the absence of contamination, and turn red at very low levels of contamination. In some embodiments, for testing a sample in which higher levels of microbial contamination are tolerated, or if the sample has been concentrated, higher amounts of biotinylated antibodies are used, and the system will be red in the absence of contamination, and turn purple at higher levels of contamination.

The foregoing description is considered as illustrative only and is not intended to limit the claimed invention. Numerous modifications and changes may readily occur to those skilled in the art. The invention is not limited to the exact construction and operation shown and described, and accordingly, all suitable modifications and equivalents are considered to fall within the scope of the invention.

We claim:

1. A method of determining whether a sample comprises a microorganism, comprising:
    A) contacting the sample with a linker, wherein the linker comprises a first functionality and a plurality of second functionalities, wherein the first functionality is capable of binding to the surface of the microorganism, wherein each of the plurality of second functionalities is capable of binding to a third functionality, and
    B) contacting the sample of step (a) with a plurality of nanoparticles, wherein each of the plurality of nanoparticles comprises a third functionality that is capable of binding to the second functionality; and
    C) detecting nanoparticle aggregation or lack thereof in the sample from (b), wherein
        the linker is added in step (a) at a concentration less than the concentration of nanoparticles and sufficient to aggregate the nanoparticles added in step (b) in the absence of microorganism , and the absence of nanoparticle aggregation in the sample indicates that the sample comprises the microorganism, or
        the linker is added in step (a) at a concentration just in excess relative to the concentration of the nanoparticles added in step (b) and the nanoparticles do not aggregate in the absence of microorganism, and the presence of nanoparticle aggregation in the sample indicates that the sample comprises the microorganism.

2. The method of claim 1, wherein the first functionality is selected from an antigen binding region of an antibody, a ligand, a receptor, a small molecule, and a lectin.

3. The method of claim 1, wherein the second functionality is selected from biotin, streptavidin, an antigen, an antibody, a ligand, a receptor, a polyhistidine tag, nickel, an aptamer, an aptamers target, trans-cyclooctene, and tetrazine.

4. The method of claim 1, wherein the third functionality is selected from biotin, streptavidin, an antigen, an antibody, a ligand, a receptor, a polyhistidine tag, nickel, an aptamer, an aptamers target, trans-cyclooctene, and tetrazine.

5. The method of claim 1, wherein the linker is an antibody and the first functionality is the antigen binding region of the antibody.

6. The method of claim 5, wherein the second functionality is biotin and the third functionality is streptavidin.

7. The method of claim 1, wherein the nanoparticles are selected from gold nanoparticles, silver nanoparticles, platinum nanoparticles, magnetite nanoparticles, gold/iron alloy nanoparticles, and latex nanoparticles.

8. The method of claim 1, wherein the target is selected from prokaryotic cells, eukaryotic cells, and parasites.

9. The method of claim 1, wherein detecting nanoparticle aggregation comprises determining at least one characteristic selected from sample color, ultraviolet-visible spectrum, ultraviolet-visible peak wavelength, and absorbance.

10. The method of claim 9, wherein the at least one characteristic of the sample from (b) is compared to at least one characteristic of a standard.

11. The method of claim 10, wherein the standard is a control reaction comprising the linker and the plurality of nanoparticles, but not the microorganism.

12. The method of claim 1, wherein the linker is added in step (a) at a concentration less than the concentration of nanoparticles and sufficient to aggregate the nanoparticles added in step (b) in the absence of microorganism, and the absence of nanoparticle aggregation in the sample indicates that the sample comprises the microorganism.

13. The method of claim 1, wherein the linker is added in step (a) at a concentration just in excess relative to the concentration of the nanoparticles added in step (b) and the nanoparticles do not aggregate in the absence of microorganism, and the presence of nanoparticle aggregation in the sample indicates that the sample comprises the microorganism.

* * * * *